United States Patent [19]

Heinig, Jr.

[11] Patent Number: 4,608,247

[45] Date of Patent: Aug. 26, 1986

[54] COMPOSITION FOR BACTERICIDAL TREATMENT OF WATER

[75] Inventor: Charles F. Heinig, Jr., Warwick, R.I.

[73] Assignee: George J. LeMire, Cranston, R.I. ; a part interest

[21] Appl. No.: 664,205

[22] Filed: Oct. 24, 1984

[51] Int. Cl.$^4$ ............................................. A01N 25/26
[52] U.S. Cl. ...................................... 424/16; 210/501; 424/132
[58] Field of Search ............... 210/668, 679, 764, 169, 210/501; 424/16, 21, 132; 427/217; 428/403, 404

[56] References Cited

U.S. PATENT DOCUMENTS

| | | | |
|---|---|---|---|
| 2,017,456 | 10/1935 | Gudmundsen | 210/501 |
| 2,521,713 | 9/1950 | Goetz | 210/764 |
| 3,268,444 | 8/1966 | Renn | 210/501 |
| 3,788,982 | 1/1974 | Zsoldos et al. | 210/679 |
| 4,092,245 | 5/1978 | Franks et al. | 210/764 |
| 4,238,334 | 12/1980 | Halbfoster | 210/679 |
| 4,353,741 | 10/1982 | Capuano et al. | 427/217 |
| 4,396,512 | 8/1983 | Beauman et al. | 210/668 |
| 4,407,865 | 10/1983 | Nice | 210/501 |

FOREIGN PATENT DOCUMENTS 2364504 8/1974 Fed. Rep. of Germany ...... 210/501
50-6718 1/1975 Japan .................................. 210/764

*Primary Examiner*—Peter Hruskoci
*Attorney, Agent, or Firm*—Salter & Michaelson

[57] ABSTRACT

A composition and method for the bactericidal treatment of water with oligodynamic metal ions. The composition comprises a particulate silver yielding material and a particulate filler material which is intermixed with the silver yielding material. The silver yielding material comprises a highly porous carrier having a hardness which is greater than that of elemental silver and a layer of elemental silver on the surfaces of the carrier, and the filler material comprises a material, such as charcoal, having a hardness which is less than that of elemental silver. The composition is utilized in accordance with the method of the invention by passing a stream of water through a quantity of the composition to cause the particles of silver yielding material to mechanically interact with each other to release silver into the water. The particles of filler material, intermixed with the silver yielding material, buffer this mechanical interaction to provide a relatively slow release of silver from the composition which can be effectively controlled so that the composition and method can be effectively used in substantially closed systems, such as swimming pool systems.

7 Claims, No Drawings

COMPOSITION FOR BACTERICIDAL TREATMENT OF WATER

BACKGROUND AND SUMMARY OF THE INVENTION

The instant invention relates to water treatment processes, and more particularly, to a novel composition for the bactericidal treatment of water.

It is widely known that chlorine can be effectively used to kill bacteria contained in water. Chlorine is commonly used for treating drinking water, and also for treating water used in swimming pool systems, and it is even used to treat waste water during sewage treatment processes. However, while the addition of chlorine to water has been found to be an effective method of killing bacteria contained in the water, it has a number of disadvantages. First, chlorine, which is a relatively volatile gas in its natural state, is rapidly dissipated from water which is left to stand open to the atmosphere, particularly when the water has a temperature of greater than approximately 70 degrees fahrenheit. Therefore, it is generally necessary to make frequent additions of chlorine to water under these conditions in order to maintain the bacteria levels in the water within safe ranges, and obviously this has disadvantages from both practical and economic standpoints. Further, while the necessity for frequently replenishing chlorine levels in water represents a major drawback to the use of chlorine for the germicidal treatment of water, there are several other disadvantages which specifically apply to the use of chlorine for the treatment of water used in open pools, such as swimming pools, hot tubs, soaking tubs and the like. In particular, chlorine produces a distinct odor as it is dissipated from an open pool of water, and this has been found to be objectionable to many swimmers and bathers. In addition, water containing high concentrations of chlorine can be harmful to the eyes of swimmers and bathers after prolonged periods of exposure and, to a lesser extent, water containing high levels of chlorine can be harmful to the skin and hair. Further, because the dissipation of chlorine from a pool of water is substantially accelerated when the water is heated to an elevated temperature level, chlorine is often dissipated so rapidly from hot tubs and soaking tubs that it is difficult or impossible to reliably maintain chlorine levels in these tubs within the desired ranges. This, combined with the fact that the growth of bacteria is substantially accelerated by elevated temperature levels, makes the use of chlorine frequently unsatisfactory for hot tub and soaking tub applications.

The use of heavy metals, in particular, heavy metals of the type commonly referred to as oligodynamic metals for the bactericidal treatment of water is also widely known. More specifically, it is known that ions of oligodynamic metals, especially silver ions, have a bactericidal effect when they are present in water, even at relatively low concentration levels, such as below 50 parts per billion. As a result, it is generally accepted that oligodynamic metal ions can be effectively utilized to maintain bacteria levels in water within tolerable ranges which permit the safe use of the water for swimming or drinking purposes. On the other hand, however, it is also recognized that excessive concentration levels of oligodynamic metal ions in water can be toxic or harmful to humans. Generally, it has also been found that silver ions are the most effective oligodynamic metal ions for the bactericidal treatment of water, and it has been found that silver ion concentration levels of up to 50 parts per billion can be safely tolerated by humans without adverse effects. Further, it has been found that silver ion concentration levels in the range of between 10 and 50 parts per billion can be generally effective for maintaining the bacteria concentrations in water within tolerable ranges. In any event, in order to utilize silver ions to effectively kill bacteria in a water treatment system, some mechanism must be provided for releasing silver ions at rates which can be effectively controlled so that the overall silver ion concentrations in the water can be maintained within a safe range of between approximately 10 and 50 parts per billion. Further, for practical reasons, it is important for a system of this type to be able to maintain the silver ion concentration level in the quantity of water within a desired range over a prolonged period of time without requiring significant amounts of attention.

While a variety of systems have been heretofore available which have utilized oligodynamic metals for the bactericidal treatment of water, generally, the heretofore known technology has failed to provide an effective means for releasing silver ions into a contained system, such as a swimming pool, at a controlled rate over a prolonged period of time. In this regard, most of the known systems have comprised apparatus which is operative for releasing silver ions at relatively high rates, but not at slow rates which can be effectively controlled over prolonged periods of time. Hence, while the known systems can be utilized for adding large quantities of silver ions to previously untreated water to kill the bacteria contained therein, they generally release silver ions at rates which are far too high for use in maintaining silver ion levels in contained or closed systems, such as swimming pool systems, after the desired ion levels have initially been reached. In many cases, this is because systems have utilized silver salts, which are highly soluble in water, as the sources of silver ions and these salts have typically released silver ions at rates which are far too high to be effectively controlled over prolonged periods in contained systems such as swimming pool, soaking tub, and hot tub systems. While water treatment systems have also been available which have utilized elemental silver which is dissolved very, very slowly in water to produce silver ions, these systems have generally not released ions at rates which are sufficient to permit their use for maintaining ion concentrations in contained systems, and generally the known systems of this type have also been ineffective for prolonged use.

The instant invention provides an effective composition and method for releasing silver ions into water at controlled practical rates over prolonged periods of time so that the composition and method can be effectively utilized in essentially closed systems. In this regard, the composition of the instant invention from which silver ions are released comprises a silver yielding material comprising a carrier having a particle size of between 4 and 20 mesh and a layer of elemental silver on the surfaces of the carrier, and a filler material also having a particle size of between 4 and 20 mesh which is intermixed with the silver yielding material. The carrier has a relatively high porocity which provides a surface area of greater than 150 square inches per gram and it has a Mohs scale hardness which is greater than that of silver, i.e. greater than 2.5. The carrier is also substantially insoluble in water having a pH of between 5 and 9. The carrier preferably consists of alumina which has a hardness of greater than 9 on the Mohs scale, a porocity which provides a surface area of approximately 210 square inches per gram, and a particle size of between 8 and 14 mesh, and preferably the alumina is activated to provide a greater bond strength between the carrier and the silver on the surfaces thereof. The silver is preferably distributed over both the interior and exterior surfaces of the porous carrier and it preferably comprises between 1% and 10% by weight of the total silver yielding material. The filler material which is intermixed with the silver yielding material has a hardness which is less than that of silver, i.e. less than 2.5 on the Mohs scale, and it is intermixed with the silver yielding material so that the ratio of filler material to silver yielding material is between approximately 1:1 and 5:1. Preferably, the filler material has a particle size which is substantially the same as that of the silver yielding material, and it is intermixed therewith in a ratio of approximately 2:1 and, preferably, the filler material consists essentially of activated charcoal.

For practicing the method of the instant invention, to treat a pool of water, a stream of water is drawn from the pool and passed through the composition of the instant invention and then returned to the pool and the flow rate of the stream is controlled to maintain the concentration of silver ions in the pool at a level of between 10 and 50 parts per billion. It has been found that because of the make-up of the composition of the instant invention, it can be effectively utilized for providing controlled additions of silver ions to a body of water at rates which are practical for most pool systems, and it has also been found that the composition can be utilized over a prolonged period of time to maintain the silver ion concentration level in a pool within a desired range. Further, because of the make-up of the composition of the instant invention and the effectiveness with which it can provide controlled releases of silver ions into a stream of water, the method and composition of the instant invention can be readily adapted for use in most conventional swimming pool and soaking tub systems. More specifically, when a quantity of the composition of the instant invention is contained in a relatively small canister, the canister can be readily utilized in a conventional swimming pool or soaking tub system simply by connecting the canister to the otherwise conventional filtration system of the swimming pool or soaking tub system. This is because the composition of the instant invention is effective for releasing silver ions to maintain the desired silver ion levels in swimming pool or soaking tub systems when relatively small quantities of the composition are exposed to water flow rates which are normally within the ranges of flow rates provided by conventional filtration system equipment. Hence, the composition and method of the instant invention can be utilized in most conventional swimming pool and soaking tub systems simply by connecting a canister containing a quantity of the composition to existing or conventional equipment of the system. This provides substantial practical advantages for the method and composition of the instant invention.

The closest prior art to the instant invention of which the applicant is aware is disclosed in the U.S. patents to Conconi (U.S. Pat. No. 2,283,883), Renn (U.S. Pat. No. 3,268,444), Nishino et al (U.S. Pat. No. 3,872,013), and Beauman et al (U.S. Pat. No. 4,396,512); the United Kingdom patents to Krause (Nos. 279,085 and 353,686), the German patent to Mitsumori et al (No. 2,505,597), and the Japanese KoKai publication No. 74 97,730 by Tsukada et al. However, none of these references suggest the combination of a relatively hard silver yielding material with a relatively soft filler material to provide a composition having the silver release properties of the composition of the instant invention. Hence, these references are felt to be of nothing more than general interest.

Accordingly, it is a primary object of the instant invention to provide an effective composition which can be utilized to release silver ions into water at a slow controlled rate in a closed system, such as a swimming pool, soaking tub, or hot tub system.

Another object of the instant invention is to provide an effective method of releasing silver ions into a pool of water which permits the overall silver ion concentration in the pool to be effectively controlled.

Another object of the instant invention is to provide an effective method of releasing silver ions into a swimming pool which permits the overall silver ion concentration in the swimming pool to be maintained at between 10 and 50 parts per billion.

An even further object of the instant invention is to provide a method of releasing silver ions into water at a slow controlled rate utilizing a silver yielding material, wherein the silver yielding material is operative over a prolonged period of time.

Other objects, features and advantages of the invention shall become apparent as the description thereof proceeds.

DESCRIPTION OF THE INVENTION

The instant invention provides an effective composition for the bactericidal treatment of water, particularly water which is contained in a closed system, such as a system comprising a swimming pool, a hot tub, a soaking tub, or the like. More specifically, the instant invention provides a composition which can be utilized in accordance with the inventive method for releasing silver ions into water at relatively slow controllable rates so that the composition and the method can be effectively utilized for maintaining the silver ion concentration level in a substantially closed system within a range of between 10 and 50 parts per billion.

The composition of the instant invention comprises a silver yielding material comprising a carrier and a layer of elemental silver on the surfaces of the carrier, and a filler material which is intermixed with the silver yielding material. The carrier has a particle size of between approximately 4 and 20 mesh, a porocity which provides a surface area of greater than 150 square inches per gram, and a Mohs scale hardness which is greater than the hardness of silver, i.e. greater than 2.5, and the carrier is substantially insoluble in water having a pH within the range of between 5 and 9. The elemental silver is deposited on the surfaces of the carrier and it is between 1% and 10% by weight of the silver yielding material. Preferably, the carrier is activated to provide an improved bond between the carrier and the silver on the surfaces thereof. The filler material also has a particle size which is between 4 and 20 mesh, and preferably, the filler material has a particle size which is substantially the same as that of the carrier. The filler material has a hardness which is less than the hardness of silver, and the filler material is also substantially insoluble in water having a pH of between 5 and 9. The volumetric ratio of filler material to carrier material is between approximately 5:1 and 1:1 and the carrier material preferably consists essentially of activated alumina, whereas the filler material preferably consists essentially of activated charcoal.

It has been found that a composition of the above type can be effectively utilized for maintaining the silver ion concentration in an essentially closed pool system within a predetermined range over a prolonged period of time. More specifically, after the silver ion concentration in a pool of water has been initially adjusted to a predetermined level by conventional means, for example, by the addition of a silver salt such as silver sulfate to the water, the composition of the instant invention can be effectively utilized to maintain the silver ion concentration level in the pool of water within the same predetermined range over a prolonged period of time. In this regard, silver ions are normally only dissipated from a pool of water when a portion of the water is removed from the pool and thereafter replaced with fresh water or when materials in which the silver ions have concentrated, such as waste materials of the type which are normally trapped in a filtration system of the pool, are removed from the pool system. Accordingly, silver ions are normally only removed or dissipated from a pool system at very slow rates and hence, in order to maintain the ion concentration level in a pool system within a predetermined ranges it is only necessary to add silver ions to the system at very slow rates. The composition and method of the instant invention are particularly adapted for use in applications of this type and they rely on the interactions of several physical and chemical characteristics of the components of the composition to provide effective controllable releases of silver ions.

It is widely known that elemental silver is only soluble in water to a very, very small degree and, in fact, it is because of this property that elemental silver is utilized in the composition of the instant invention instead of other forms of silver, such as silver salts, etc. However, while the solubility of elemental silver is of some significance in the instant invention, the physical interactions between the particles in the composition also play a significant role in providing an effective ion release from the composition of the instant invention. Specifically, when water passes through the particles of the composition of the instant invention, silver is released chemically as it is slowly dissolved in the water, but silver is also released mechanically in the form of tiny elemental silver particles which are so small that they are rapidly also dissolved in the water and become ionized. This mechanical release of silver results from the combined effects of abrasion and erosion as water is passed through the composition. In this regard, since the carrier has a hardness which is greater than the hardness of silver, and also greater than the hardness of the filler material, the carrier remains substantially intact throughout this abrasion and erosion process, whereas the silver is eroded and abraded from the surfaces of the carrier as the water passes over the particles and adjacent silver yielding particles contact one another. On the other hand, since the filler material which is intermixed with the silver yielding material has a hardness which is less than that of silver, i.e. it is less than 2.5 on the Mohs scale, the filler material provides a cushioning effect which retards the release of silver by preventing many of the particles of silver yielding material from physically interacting with each other. Hence, by providing a silver yielding material comprising a carrier having a hardness which is greater than that of silver, and by intermixing the silver yielding material with a filler material having a hardness which is less than that of silver, a controlled abrasion and erosion reaction can be achieved when water is passed through the composition to effectively control the mechanical release of silver. The high porocity of the carrier not only provides a high surface area for the silver, but it also retards the release of silver because a substantial portion of the silver on the carrier is on the interior surfaces thereof, and this portion of the silver is more protected from release by erosion and abrasion than the silver on the exterior surfaces. To achieve the optimum result, the particle sizes of the silver yielding material and the filler material are preferably substantially the same so that the desired interaction between the particles is achieved and the ratio of filler material to silver yielding material is between approximately 1:1 to 5:1 to achieve the desired interaction. In addition, the particle sizes of both the filler material and the silver yielding material must be within the range of between 4 and 20 mesh to both achieve the desired particle interaction and also to provide a material through which water can easily flow.

Preferably, the carrier comprises activated alumina which, because of its high degree of hardness (greater than 9 on the Mohs scale) and because of its high porocity which provides a surface area of approximately 210 square inches per gram, provides a highly effective transport medium for the silver. Preferably, the alumina is activated by heating it to a temperature of greater than approximately 400 degrees fahrenheit to provide an improved bond between the alumina and the silver and preferably the filler material comprises charcoal, in particular, activated charcoal, since activated charcoal is substantially softer than silver and it also has a number of well-known absorption properties which make it particularly desirable for use in a water treatment system.

EXAMPLE

An outdoor swimming pool system comprising a private swimming pool containing approximately 19,000 gallons of water was treated over a period of approximately three and a half (3½) months utilizing the composition and method of the instant invention. The system included a conventional diatomaceous earth filter and a canister containing the composition of the instant invention which were both fed by a single filtration pump. The canister, which was approximately four inches in diameter and twenty inches in length and which had a central open tubular passage therethrough of approximately one inch in diameter, was filled with the composition of the instant invention in the area of the canister between the outer wall thereof and the open tubular passage. Water was introduced into the canister so that it could either flow through the central tubular passage or through the composition and the overall flow rate of water through the canister was maintained at approximately 15 gallons per minute over the three and a half month period. The composition utilized consisted essentially of a silver yielding material having a carrier of alumina with a particle size of between 5 and 14 mesh, and a layer of elemental silver on the surfaces of the carrier, the silver comprising approximately 1.25 weight percent of the silver yielding material. The silver yielding material had been prepared by a conventional silver refining process to provide a layer of elemental silver on the surfaces of the alumina medium and thereafter the alumina with silver on the surfaces thereof had been heated to a temperature of approximately 400 degrees fahrenheit to activate the alumina. Approximately 1,000 grams of silver yielding material was intermixed with approximately 660 grams of activated charcoal having a particle size of between 5 and 14 mesh to provide an approximate volumetric ratio of two parts charcoal to one part silver yielding material in the composition which was utilized in the canister. Initially, before the canister was operated, the water in the pool was adjusted to provide a silver ion concentration level of approximately 20 parts per billion utilizing a silver sulfate composition. Thereafter, the silver ion concentration level in the pool was maintained exclusively through the release of silver ions from the composition of the instant invention in the canister. Over the three and a half month period, the water temperature in the pool was generally between 70 and 85 degrees fahrenheit, and the bather load was considered to be moderate. The pool was operated out of doors and the amount of rainwater which entered the pool was considered to be moderate. The diatomaceous earth filter was backflushed approximately monthly. It was found that throughout the entire period, the silver ion concentration in the pool system was maintained within the range of between 10 and 25 parts per billion. In this regard, it was found that after a period of approximately one week, the ion concentration level had dropped from its initial value of approximately 20 parts per billion to a level of approximately 10 parts per billion, and thereafter a level of approximately 10 parts per billion was consistently maintained throughout the period. Water samples were removed from the surface portion of the pool on a weekly basis and tested for coliform bacteria levels. It was found that throughout the period the coliform level was less than one organism per hundred milliliters of pool water. This level of coliform bacteria was considered to be extremely satisfactory, and hence the quality of water in the pool was considered to be extremely safe for swimming purposes. It was found, however, that at the end of the three and one-half month period the silver had been substantially depleted from the surfaces of the silver yielding material. When the system was operated beyond the period without changing the canister, the silver ion concentration level in the pool dropped effectively to nil, and upon testing after operating for approximately two weeks under these conditions, it was found that the coliform level had climbed to 16 organisms per 100 milliliters of water. Hence, it was concluded that the composition and method of the instant invention had effectively operated throughout the three and one-half month period, and that they had effectively released silver ions to provide a germicidal effect in the pool which maintained the bacteria level therein within safe and tolerable levels. However, once the silver had been depleted from the canister, the silver ion concentration level in the pool decreased rapidly and the water in the pool could no longer be considered safe for swimming.

As this invention may be embodied in several forms without departing from the spirit or essential characteristics thereof, the present embodiment is therefore illustrative and not restrictive, since the scope of the invention is defined by the appended claims rather than by the description preceding them, and all changes that fall within the metes and bounds of the claims or that form their functional as well as conjointly cooperative equivalents, are therefore intended to be embraced by these claims.

What is claimed is:

1. A composition for the bactericidal treatment of a stream of water comprising:
   a. a particulate silver yielding material comprising:
      i. a carrier which has a particle size of between approximately 4 and 20 mesh, a surface area of greater than approximately 150 square inches per gram, and a Mohs scale hardness of greater than 2.5 and which is substantially insoluble in water having a pH of between 5 and 9;
      ii. a layer of elemental silver on the surfaces of said carrier, said silver being between approximately 1% and 10% by weight of said silver yielding material; and
      iii. the mechanical interaction between adjacent particles of said silver yielding material causing a release of elemental silver into said stream when it is passed therethrough;
   b. a particulate filler material intermixed with said silver yielding material, said filler material being substantially insoluble in water having a pH of between 5 and 9, said filler material having a particle size of between approximately 4 and 20 mesh and a Mohs scale hardness of less than 2.5, the volumetric ratio of said filler material to said silver yielding material being between approximately 1:1 and 5:1; and
   c. said filler material reducing the rate at which elemental silver is released from said composition to produce a controlled release of said elemental silver when said stream is passed therethrough.

2. In the composition of claim 1, said carrier further characterized as being activated.

3. In the composition of claim 2, said carrier comprising alumina.

4. In the composition of claim 1, said carrier comprising alumina.

5. In the composition of claim 4, said filler material comprising charcoal.

6. In the composition of claim 1, said silver yielding material and said filler material being of substantially the same particle size.

7. The composition of claim 1 further characterized as being substantially free from silver salts.

* * * * *